United States Patent [19]

Gupta

[11] Patent Number: 4,801,760
[45] Date of Patent: Jan. 31, 1989

[54] TERTIARY BUTYL ALCOHOL PURIFICATION

[75] Inventor: Vijai P. Gupta, Berwyn, Pa.
[73] Assignee: Arco Chemical Company, Newtown Square, Pa.
[21] Appl. No.: 155,411
[22] Filed: Feb. 12, 1988
[51] Int. Cl.$^4$ .................... C07C 29/78; C07C 31/12
[52] U.S. Cl. .................................................. 568/923
[58] Field of Search ........................................ 568/923

[56] References Cited

U.S. PATENT DOCUMENTS

| | | | |
|---|---|---|---|
| 2,809,884 | 10/1957 | Ratje | 568/923 |
| 3,052,700 | 9/1962 | Waldmann et al. | 568/923 |
| 3,870,735 | 3/1975 | Stein et al. | 568/923 |

FOREIGN PATENT DOCUMENTS

| | | | |
|---|---|---|---|
| 1107659 | 5/1961 | Fed. Rep. of Germany | 568/923 |
| 5659 | 5/1963 | Japan | 568/923 |
| 754551 | 8/1956 | United Kingdom | 568/923 |

*Primary Examiner*—J. E. Evans
*Attorney, Agent, or Firm*—William C. Long

[57] ABSTRACT

The invention relates to recovery of high purity TBA from a mixture with organic impurities whereby water in amount of 1 to 5 wt % is incorporated in the mixture and pure TBA crystals are separated upon cooling and crystallization.

5 Claims, 1 Drawing Sheet

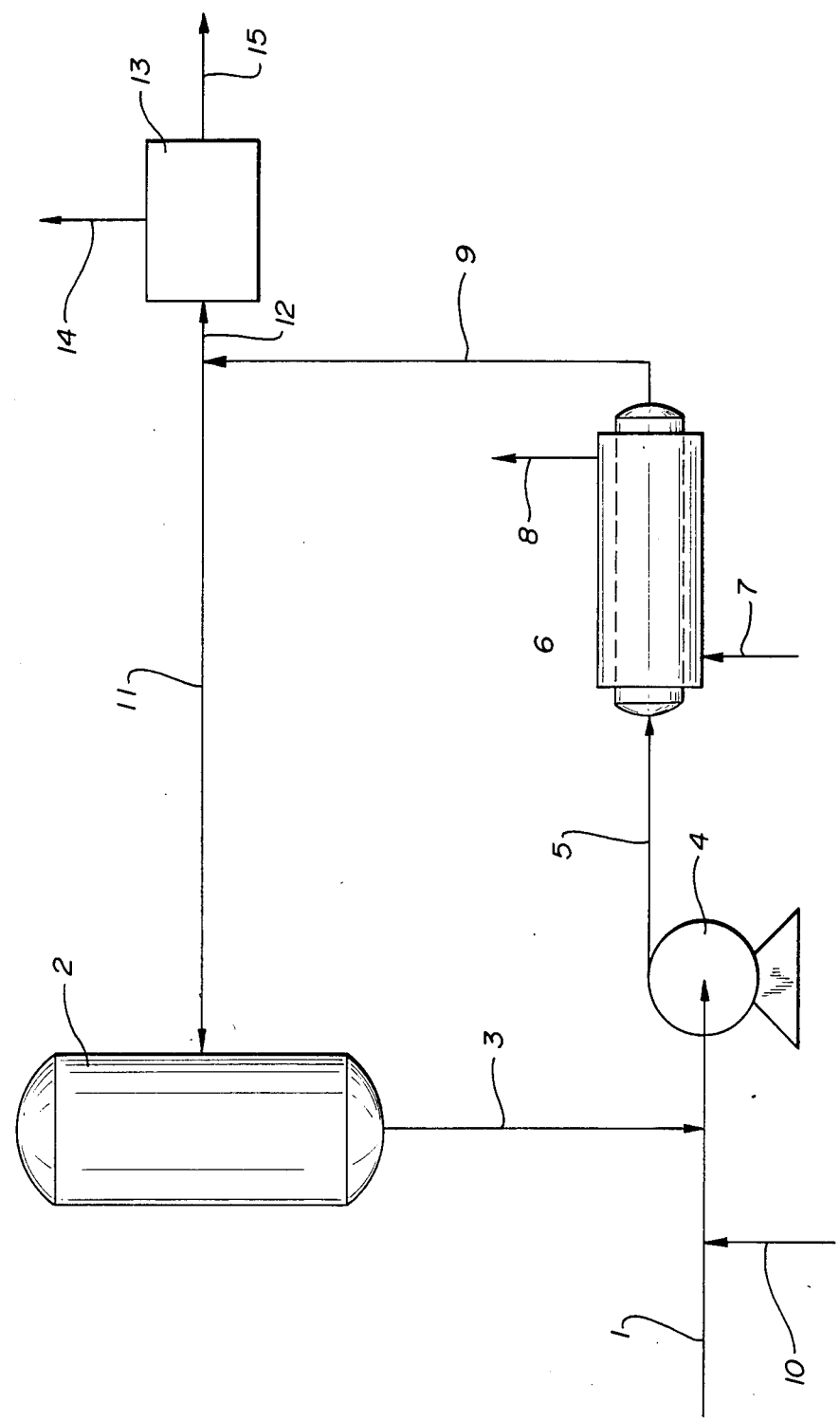

TERTIARY BUTYL ALCOHOL PURIFICATION

FIELD OF THE INVENTION

The present invention relates to a process for the separation and recovery of high purity tertiary butyl alcohol by crystallization.

DESCRIPTION OF THE PRIOR ART

Tertiary butyl alcohol (TBA) is an important chemical of commerce which has utility in the manufacture of tertiary butyl chloride and in the manufacture of tertiary butyl phenol. In the field of synthetic perfumes, tertiary butyl alcohol is an important raw material for the preparation of artificial musk. It is an authorized denaturant for use in proprietary ethanol mixtures as well as in several specialty denatured alcohols. It is used in the production of isobutylene, and the like.

TBA is widely produced by the oxidation of isobutane or from tertiary butyl hydroperoxide as a result of reaction with an olefin whereby an oxirane compound such as propylene oxide is formed and the tertiary butyl hydroperoxide is converted to TBA. It is also produce by the hydration of isobutylene.

TBA which is produced commercially from isobutane oxidation to the hydroperoxide normally has associated with it substantial quantities of organic impurities such as acetone, isopropanol, methyl t-butyl ether, MEK, t-butyl formate, and the like which are difficult to separate.

Distillation techniques are effective to some extent in separating impurities but due to the close boiling points of materials such as isopropanol it is not practical to separate and recover very high purity TBA by distillation.

Crystallization procedures likewise have not proven practically effective. Crude TBA undergoes a complete phase change from liquid to solid over just a few degrees of cooling leaving little or no mother liquor for separation. The impurities are then not readily separable and mechanical problems are caused by the rapid phase change. To produce a crystal slurry that can flow freely requires very accurate temperature control as even very small temperature changes will sharply increase or decrease the crystal concentration. In addition, under such circumstances cooling surfaces are likely to foul or even plug. Crystals of TBA which ar produced are at a temperature very close to the melting point of pure TBA and in the process of separation, as by centrifugation, crystals melt because of energy input and are rejected with the mother liquor.

SUMMARY OF THE INVENTION

It has now been found that the addition of small quantities of water to TBA which has organic impurities associated with it strongly depresses the freezing point of the mixture such that the mixture can be cooled substantially below the TBA freezing point with formation of a free flowing slurry containing substantially pure TBA crystals which are essentially free of the added water. Because the crystals are considerably below their melting point they can readily be separated without loss. The wide temperature window between initial crystal formation and thick slurry formation makes slurry density much less sensitive to temperature thus alleviating the necessity for very accurate temperature control.

BRIEF DESCRIPTION OF THE DRAWING

The accompanying drawing illustrates in schematic form practice of the invention.

DETAILED DESCRIPTION

The present invention is generally applicable to mixtures of TBA together with minor quantities, eg. up to about 15% by weight, of organic impurities. In case of crude TBA with higher concentrations of organic impurities, it will generally be easier to reduce such impurities to under 15% via distillation. The invention is especially applicable to TBA product streams which are recovered from the epoxidation of olefins such as propylene by reaction with tertiary butyl hydroperoxide. These latter TBA streams usually contain at least 90% TBA and preferably contain at least 95% TBA. Higher purity streams, eg. those containing 99% or more TBA are also advantageously treated by the invention.

The commercial TBA streams contain such organic impurities as are normally produced by the method by which the TBA is formed. Included among such impurities are acetone, isopropanol, isobutylene oxide, MTBE, MEK, sec-butyl alcohol, t-butyl formate, t-butyl acetate, isobutyl formate, and the like. Slight amounts of water may also be contained therein.

In accordance with the invention, the water content of the TBA mixture is adjusted to provide at least 1%, and preferably at least 2% by weight water in the mixture. It is preferred that the amount of water not exceed 5% by weight in the mixture since the effectiveness of water to depress the freezing point decreases rapidly above 5%. Most desirably, the amount of water should not exceed 4% by weight in the mixture. This resulting mixture is then cooled to a temperature at which a freely flowing slurry of high purity TBA crystals in liquid mother liquor is formed. It is advantageous to cool the mixture significantly below the freezing point of TBA (25.5° C.) so that separation of TBA crystals can be readily accomplished, but not so low that the slurry becomes too thick to flow or approaches solid state. Generally cooling to a temperature in the range 0° to 20° C., preferably 5° to 15° C. is most advantageous.

Crystallization and separation of the high purity TBA crystals can be carried out in conventional apparatus. Th separated crystals can be washed with crystal melt to further enhance purity.

The invention can be further described with reference to the attached drawing.

The stream of TBA which is contaminiated with minor amounts of organic impurities passes via line 1 and is admixed with water which is introduced via line 10 in amount suffioient to provide at least 1% by weiqht water in the resulting admixture. Perferably, sufficient water is added to provide 2%–4% by weight water in the admixture; addition of water to form mixtures containing more than 5 wt % water is not preferred.

The mixture of TBA, organic impurities and water is combined with circulating crystallizer slurry which passes from hold tank 2 via line 3 and the combined materials pass to pump 4 and then via line 5 to scraped surface heat exchanger 6 wherein TBA in extremely high purity is crystallized. As above indicated, the mixture in heat exchanger 6 is cooled to 0° C. to 20° C., preferably 5° C. to 15° C. for best results. The coolant is introduced to exchanger 6 via line 7 and removed via line 8 after indirect heat exchange with the TBA mixture.

The slurry from exchanger 6 is removed via line 9. The bulk passes via line 11 to the hold tank 2 and from there it is cycled to the heat exchanger as above described. This cyclic operation is advantageous in order that appropriate crystal growth be achieved.

An amount of slurry equivalent to the net feed of impure TBA via line 1 and water via line 10 is passed via line 12 to separation zone 13, preferably a centrifugal separator, where mother liquor is separated via line 14 and the high purity crystals of TBA are recovered via line 15.

Other separation means such as filters and the like can be used in place of centrifugation to separate pure TBA crystals from mother liquor. The mother liquor can advantageously be used in applications where very high TBA purity is not necessary, e.g., as gasoline additive.

The TBA crystals can be washed as with crystal melt for further enhancement of purity.

The following examples illustrate the invention.

COMPARATIVE EXAMPLE A

TBA associated with minor amounts of organic impurities was cooled with agitation to determine the crystallization characteristics. The TBA mixture had the following composition:

TABLE A

| Component | Wt. % |
|---|---|
| TBA | 94.4 |
| Acetone | 0.5 |
| Isopropanol | 0.3 |
| Isobutylene Oxide | 1.9 |
| Methyl t-Butyl Ether | 0.2 |
| Methyl Ethyl Ketone | 0.5 |
| Sec-Butyl Alcohol | 0.3 |
| t-Butyl Formate | 0.4 |
| Iso-Butyl Formate | 0.3 |
| t-Butyl Acetate | 0.4 |
| Water | 0.1 |
| Others | 0.7 |

Upon cooling, the mixture became cloudy with a trace of crystals at 20° C.; at 18.5° C. a very thick slurry had formed which impeded the agitator.

The comparative example demonstrates the narrow temperature range between the beginning of crystallization and the formation of thick, substantially unmanageable slurry which has rendered crystallization an impractical way to recover high purity TBA by conventional methods.

EXAMPLE 1

A mixture was formed of TBA with minor amounts of organic impurities and containing 2.7 wt. % water. The mixture was crystallized in a forced circulation crystallizer, with the first crystals appearing at about 12° C. A temperature of 10° C. was maintained with a temperature differential of about 5° C. between crystallization liquor and cooling water.

A free flowing slurry of 12% by wt. high purity TBA crystals in mother liquor was obtained. The crystals were separated by centrifugation and analyzed without washing. Washing the crystals with crystal melt to reduce the adhering mother liquor further improves purity. The following table shows the composition of the feed, the crystal melt, and the mother liquor:

TABLE 1

| Component | Feed | Crystal Melt | Mother Liquor |
|---|---|---|---|
| $H_2O$ | 2.7 | 0.08 | 3.6** |
| TBA | 94.3 | 99.83 | 94.1 |
| MeOH | 0.5 | 0.002 | 0.206 |
| Me Formate | 0.86 | — | |
| Acetone | 0.37 | — | 0.39 |
| IPA | 0.32 | 0.074 | 0.37 |
| MEK | 0.17 | — | 0.17 |
| TB Formate | 0.17 | 0.006 | 0.21 |
| SB Formate | 0.05 | — | 0.06 |
| IB Formate | 0.21 | 0.003 | 0.29 |
| Others | 0.34 | 0.001 | 0.60 |

**Some moisture pick up.

These results demonstrate that high purity TBA is readily recovered by crystallization from mixtures with organic impurities through practice of this invention. It should be noted that the added water does not co-crystallize in the TBA crystals.

I claim:

1. The method of recovering tertiary butyl alcohol of improve purity from mixtures which also contain minor amounts of organic impurities which comprises:
   (a) forming an admixture of tertiary butyl alcohol containing minor amounts of organic impurities, and 1 to 5 wt % water,
   (b) cooling said admixture to a temperature sufficiently low to form a slurry containing tertiary butyl alcohol crystals in mother liquor, and
   (c) separating said tertiary butyl alcohol crystals from said mother liquor.

2. The method of claim 1 wherein said admixture is cooled to a temperature above 0° C. and below 20° C.

3. The method of claim 1 wherein said admixture is cooled to a temperature above 5° C. and below 15° C.

4. The method of claim 1 wherein the said admixture of (a) comprises 2 to 4 wt % water.

5. The method of claim 1 wherein the tertiary butyl alcohol starting mixture contains at least 95% by weight tertiary butyl alcohol.

* * * * *